United States Patent [19]
Spitzer

[11] Patent Number: 6,022,348
[45] Date of Patent: Feb. 8, 2000

[54] CLAMPING CONNECTION FOR MEDICAL EQUIPMENT AND APPARATUS

[76] Inventor: Daniel Spitzer, Anna-Schneider-Weg 5, 07545, Gera, Germany

[21] Appl. No.: 09/201,187

[22] Filed: Nov. 30, 1998

[30] Foreign Application Priority Data

Nov. 30, 1997 [EP] European Pat. Off. ............. 97121037

[51] Int. Cl.⁷ .................................................. A61B 17/56
[52] U.S. Cl. ................................ 606/54; 606/53; 606/59; 606/72
[58] Field of Search ................................. 606/53, 54, 55, 606/56, 57, 58, 59, 60, 61, 72, 73, 1

[56] References Cited

U.S. PATENT DOCUMENTS 5,190,541  3/1993  Abele et al. ............................... 606/46

Primary Examiner—Michael Buiz
Assistant Examiner—David O. Reip
Attorney, Agent, or Firm—Horst M. Kasper

[57] ABSTRACT

The invention relates to a coupling of two sides of a synergetically cooperating fixation system in medical equipment and apparatus, illustrated by way of example of an external fixator with rod-like guide elements, wherein a point-precise and internally tension-free clamping connection is formed by in each case two planar parallel disposed faces. The complementary, uncoated coupling surface is shape-matchingly impressed "de novo" and "uniquely" during each coupling closure by a static press-on force based on a diamond, plastic grain layer of a chaotic profile solidly attached to one of the faces, such that a clamping connection with the multilatent force-form match closure is furnished.

28 Claims, 5 Drawing Sheets

6,022,348

CLAMPING CONNECTION FOR MEDICAL EQUIPMENT AND APPARATUS

BACKGROUND OF THE INVENTION

1. Field of the Invention

The invention relates to a clamping connection for medical equipment and apparatus, illustrated by way of an external fixator with a fixation frame made of guide rods. Fixators of this kind require a mechanical connection between the guide rods and the screws according to Schanz, which has to assure a synergetic compatibility of these system sides under all medical and functional aspects. A direct access to a multi-axes and unlimited movability with an internally tension-free, point-precise and solid coupling of guide rods of the fixation frame and of the screws according to Schanz is the central criteria for such clamping connections.

2. Brief Description of the Background of the Invention Including Prior Art

The requirements to be imposed on such a coupling result also predominantly from the medical indication of the external fixator. Thus, the external bone fracture treatment with screws according to Schanz is indicated in case of a I.–III. grade open fracture, since the external bone fracture treatment represents a quick and in particular minimally invasive and thus biological method, which additionally iatrogenically traumatizes and injures as little as possible the all decisive remaining vascularization of the damaged limb.

Since the osteosynthesis method of the external fixator in addition allows continuously available inter-fractural interventions such as compression, distraction, neutralization and dynamization of the repositioned fracture, the osteosynthesis is initially considered far more than only an alternative because of the remote position relative to the fracture of the stabilizing elements and because of the minimized invasiveness.

Indispensable constructive and functional requirements are derived therefrom for the external fixator.

The phase of the consolidation of the bone fracture requires initially an absolutely immobile retention of the repositioning result, since motions of the fragments lead to further soft tissue injuries and vascularization injuries. This is initially also possible with a fixator construction which contains internal tensions and is neutral in its sum. However, these system-internal forces begin to generate effects in the course of the treatment, which are primarily noticeable at the bone contact zone of the screws according to Schanz. Tension-induced interferences of the osseous microcirculation effect local bone resorption up to the sequestration with a consecutive loosening of the screws according to Schanz and obligatory and perpetualizing inflammation reaction as a pacemaker from a soft tissue infection up to osteomyelitis. Furthermore, a loss of the anchoring of the screw in case of a generally not yet bone-consolidated fracture is also associated with a failure of the osteosynthesis.

The external fixator of this kind has to allow in addition a pressure stimulation by a dynamization with a partial abandonment of the strictly axial fixation components for a procedural acceleration of the interfractural configuration. The two qualities however cannot be reliably realized without a reliable starting position of an internal, tension-neutral primary fixation. Also other procedural bone position changes or bone position corrections are subject to adequate requirements for the external fixator.

The constructions known in the art meet these requirements however only to an insufficient degree. Additional public and controversial concepts relating to a change in procedure toward an internal osteosynthesis after soft tissue consolidation or the use of an external fixator as an initial and definite osteosynthesis method show this.

Mechanical clamping connections of components and of component surfaces in a synergetic incompatible constellation are the prevailing state-of-the-art also in connection with medical equipment and apparatus of completely different dimension such as, for example, operating tables. Thus, various devices of the operating table function with shape-matching profiled couplings for the purpose of a preoperative positional manipulation of the patient, where the profiled couplings are furnished with an extremely coarse thread or subdivision based on the potential mass-determined requirements. The thereby unavoidable coarse positional offset of the two coupling sides causes incompatible malpositionings of the patient. A desirable sensitive and delicate, precise primary adjustment, as well as in particular also necessary acute changes or corrections during the operation, are therefore not possible. The inadequate provisional measures employed as countermeasures mean not only widely applied practical disadvantages of the operational handling, but are in addition not acceptable as a matter of principle.

The requirement for a point-precise and internally force-neutral fixation and defixation under minimal closure torques and opening torques, as well as simultaneously minimized closure paths and opening paths, holds therefore for clamping connections of medical instruments, medical equipment, and medical apparatus of the recited kind, wherein the general requirements for low proper mass and construction size, for simplicity and durable functional reliability, low wear or practically wear free, for biologically lasting compatibility as well as clinical unproblematic capability of manipulation continue without limitation.

The very sensitive and central problem, which has hitherto been completely unsatisfactorily treated and/or neglected in connection with these medical equipment and apparatus, thus continues to exist in the apparently unresolvable goal conflict on the side of the equipment relating to the physical connection between force and path; in the present case especially in connection with a coupling-forming static pairing of two mechanical components solely by their surfaces.

A force-matching-dependent coupling pairing of two completely smooth and unprofiled faces offers apparently an ideally precise and motion-free fixation while having the smallest closure path and opening path. This force-matching dependent coupling pairing requires however a completely impracticable large closure torque and opening torque for achieving a sufficient loadability, whereby finally even the immediate coupling pair itself loses again increasingly in quality.

The state of the art shows in a similar context a geometrically-caused relative increase in the size of the pair surface in the form of a ball-shaped body according to the European printed patent document EP 0 490 812 B1 (claims 6 and 7 as well as drawing, FIGS. 1–13), wherein one of the surfaces carries in addition a material-proper profile based on so-called bolting fibers, or alternatively, an anti-sliding coating. The two measures improve in fact the adhesion of the two pairing surfaces relative to which other, which however shows only that the designated hinge coupling is forced-matchingly constructed. Relatively high closure forces and opening forces as well as a relatively large volume of components carrying the coupling surfaces remain therefore in principle indispensable.

In this connection, a device for the external fixation of bone fragments has become known from the German printed patent document DE-OS 37 22 595 A1, which device considerably reduces the undesired clamping resistance of the movable and lockable telescope, operating as guiding columns of the fixator, based on surface hard-material coatings of an extraordinarily high hardness and low frictional coefficient, wherein a diamond-type carbon coating is proposed for this purpose in claims 1 and 2. This patent reference as well is clearly directed to the generally valid, urgent basic requirement for a reasonable, sensible kinematic, adjustable and effective, "well-running" fixator which would prevent jolt-like motions which could by all means lead to new injuries in the region of the fracture and which can impair, deteriorate, and worsen the healing process.

An important goal of the proposal according to German printed patent document DE-OS 37 22 595 is therefore a reliable and controlled readjustment of the fixator under compression load, which is only possible under stable low internal friction influence. The implicit essential aspect overlaying this is that the diamond hard-material coating is employed here for a decrease of the internal friction of the sliding surfaces of medical equipment and apparatus, which exhibits a broad competing spectrum of application of diamond coatings without a favorable priority. Furthermore, shape-matching pairings of surfaces, which furnish a relatively solid and visually controllable coupling connection based on profiles, formed on two sides like wedge teeth and disposed engaging each other on opposite sides, are still widely employed in clinical practice. Objectionably large closure paths and opening paths are required here by the relatively small, even though practically very differentiated closure forces and opening forces depending on the profile depths and the flank angle of the profiling, wherein the objectionable large closure paths and opening paths are additionally and regularly associated with an offset angle of the coupling surfaces both during the fixation as well as in particular during the defixation up to a size of a full profile spacing. Compare PCT WO 92/13496, FIGS. 3 and 4; in addition DE-OS 38 02 833 A1, FIG. 2 as well as column 3: "toothed annular face 17" as well as in particular journal: OP-Journal No. 3, Volume 11, December 1995, p. 373, SYNTHES, pictures to "the small fixator".

A pure force matching with a shape-matching component is in addition expressly indicated in the German printed patent document DE-PS 37 27 400 C1 in connection with the fixation of tangentially disposed cylindrical rods with outer threads, column 2, lines 13–28, which represents merely a geometrically critical tensioning of peripheral thread sections according to the solution of FIGS. 1 and 2. Therefore, the express claim of German Patent DE-PS 37 27 400 C1 remains uncovered in the solution provided.

All previously recited, subdivision-caused form-matching connections operate in fact sufficiently under the influence of a legitimate external load, they are however completely incapable to enter such a shape-matching coupling under the exclusion of illegitimate, coupling-internally induced loads.

A human medical compatibility of these engagement dependent, shape-matching couplings is therefore in general not recognizable for a surgical primary fixation in the course of a repositioning, such as in particular as sensitive defixation in the course of a postoperative dynamization, based on the already described claim of internal tension-free and point-precise coupling.

Therefore it appears to be imperative to define and to satisfy by way of invention an apparently buried requirement of the state of the art.

All previously described solutions of the state of the art are compromise-oriented selection decisions relative to their closure configuration, which selection decisions are characterized by nature by an equipment-specific weighing of the available functional criteria and technical parameters and which therefore deliver neither a generally satisfying solution nor a recognizable concrete suggestion for a qualitatively advancing new solution.

According to a more remote connection with the present invention, reference is made to long known, manual gripper instruments, such as two-armed tweezers for medical, in particular, surgical purposes, where the inner sides of the tweezers are covered with a diamond grain layer for improving the adhesion capabilities and the gripping capabilities as well as for a decrease of the subjective support force and cohesion. Already the German petit patent DE-Gbm 1 794 844 shows tweezers for medical use, wherein the inner faces of the front ends of the arms exhibit a diamond application or similar roughening.

The German printed patent document DE-OS 32 01 616 A1 describes foreign-body tweezers with two gripper tips plated or coated with the diamond dust in order to remove foreign bodies, in particular glass pieces or glass splinters, easily and with a light, minimal hand motion from the body of a human being or of an animal. Similar pronouncements are also contained in the German petit patent DE-Gbm 84 06 785.3 for tweezers for surgical and cosmetic purposes. Finally, the German petit patent DE-Gbm 85 12 734.5 describes precision tweezers, wherein at least one of the oppositely disposed jaw inner sides is formed with a grain layer of diamonds or of cubic crystalline boron nitride in a region of its clamping zones, in order to exceed the clamping effect of mechanical roughnesses and in order to penetrate with the grain tips into the surface of the object to be fixed or gripped. The extraction of teeth and of roots of teeth, as well as a removal of tissue, a removal of foreign bodies, and osteopathic surgical procedures are mentioned in this connection. Finally, the German petite patent concludes that the novel coating of the mouth of the tweezers in the region of the clamping zone is important for a secure and injury-free fixation of a part to be gripped.

Thus, it is common to all the recited instruments, that their two coated gripper arms are movable approximately within the arcuate measure of a preferably common swivel radius, and that the gripper arms form a tangent nearly planar parallel to the surface of an independent, regular non-metallic third body in a final operation position or temporarily penetrate the third body with their grain layer from two sides, in order to release the third body after a manual manipulation. A direct and immediate pairing of faces of the two coated metallic inner sides, which leaves the stated principle of an instrumental gripper coupling, is both strange and valueless in this context suggesting the concrete purpose determination of the tweezers. In addition, a direct and immediate face pairing is additionally technically without effect based on a two-sided coating of the arms, relative elastic arm cross-sections, as well as labile and not play-free swivel center points of the arms. Such further considerations relating to a radical reduction of the described function principle of coated gripper arms of tweezers in the sense of a static pairing of faces of their coated surfaces, possibly by a necessarily replacementless elimination of the independent gripper object itself, are therefore not only not suggested, but instead already suppressed or refuted in their premises.

The access to such, up to now unknown, aspects of diamond-coated plane-parallel surfaces at all, is therefore only possible by way of a not patent-preventing "ex-post facto analysis" under substantial incorporation of the present invention.

SUMMARY OF THE INVENTION

1. Purposes of the Invention

It is an object of the present invention to eliminate in a surprisingly simple and complete way the specific disadvantages associated with the state of the art by a newly defined clamping connection comprising an endlessly repeatable, point-precise force and form matching of complementary metallic surfaces, without giving up the selected advantages associated with the state of the art.

These and other objects and advantages of the present invention will be come evident from the description which follows.

2. Brief Description of the Invention

In accordance with the present invention, there is provided for a clamping connection for medical supports. A first coupling disk has a three-dimensional grain layer of diamond or crystalline boron nitride solidly attached to an engaging metallic face of the first coupling disk, furnishing a first surface of the first coupling disk. A second coupling disk lacks a three-dimensional grain layer of diamond or crystalline boron nitride solidly attached to a second engaging metallic face of the second coupling disk. Said first coupling disk with the first surface faces the second engaging metallic face of the second coupling disk such that the coupling disks are undividedly force-matching based on the first surface facing the second engaging metallic face and in that the second engaging metallic face assumes temporarily a respective plastic inversion profile of the three-dimensional grain layer of the first surface. The immediately oppositely disposed first coupling disk and second coupling disk are simultaneously undividedly shape-matchingly coupling forming based on external static clamping forces pressing the first coupling disk against the second coupling disk and form a multilatent static impression coupling with an undivided force-form match.

The immediately oppositely disposed first surface of the first coupling disk and the second engaging metallic face of the second coupling disk can be disposed constantly planar parallel relative to each other.

The first surfaces of the first coupling disk can be formed planar and without profile. The second engaging metallic face of the second coupling disk can be formed planar and without profile.

The first surface of the first coupling disk and the second engaging metallic face of the second coupling disk can in each case be formed as an annular ring. The annular ring-shaped surface of the first coupling disk and of the second coupling disk can in each case exhibit a centered inner collar. A compression spring element can be supported in the centered inner collar and press perpendicular to a surface plane. An untensioned axial length of the compression spring element can be larger than an axial length of the centered inner collar.

The three-dimensional grain layer of the first coupling disk can exhibit a larger hardness than an uncoated surface of the second coupling disk. The three-dimensional grain layer can exhibit a three-dimensional surface having a chaotic structure.

Mechanical means can be connected to the first coupling disk and to a first coupling side and mechanical means can be connected to the second coupling disk and to a first coupling side. A position of the mechanical means can be determined by the coupling forming first coupling disk and second coupling disk.

The mechanical means can be formed of open clamping jaws. Cylindrical guide rods can be fixed and attached in the open clamping jaws parallel to a coupling plane. Screws according to Schanz can be fixed and attached in the open clamping jaws parallel to a coupling plane.

The mechanical means can be formed of open half boreholes. Cylindrical guide rods can be fixed and attached in the open half boreholes parallel to a coupling plane. Screws according to Schanz can be fixed and attached in the open half boreholes parallel to a coupling plane.

Mechanical means delivering a static clamping force directed to the first coupling disk and the second coupling disk can be disposed facing each other. The mechanical means can be disposed perpendicular to a plane of engaging faces of the coupling disks.

Mechanical means can cooperate with the cylindrical stay bolt. A closure nut can be supported at the cylindrical stay bolt.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

In the accompanying drawings, in which are shown several of the various possible embodiments of the present invention.

DESCRIPTION OF THE INVENTION AND PREFERRED EMBODIMENTS

Figure 3:
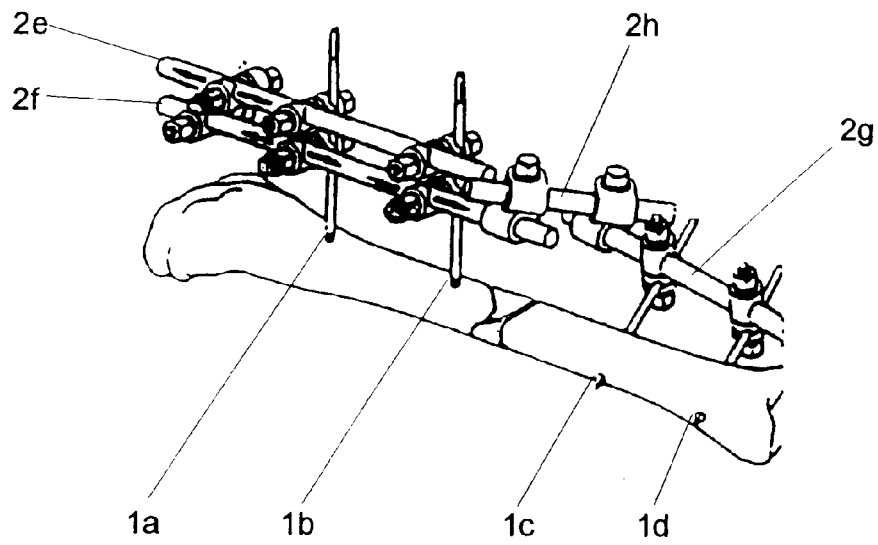
FIG. 3 shows a number of like clamping connections of an external fixator with a fixed final position of the screws according to Schanz at a fragment and cylindrical guide rods positioned relative to the clamping connections.
Figure 1:
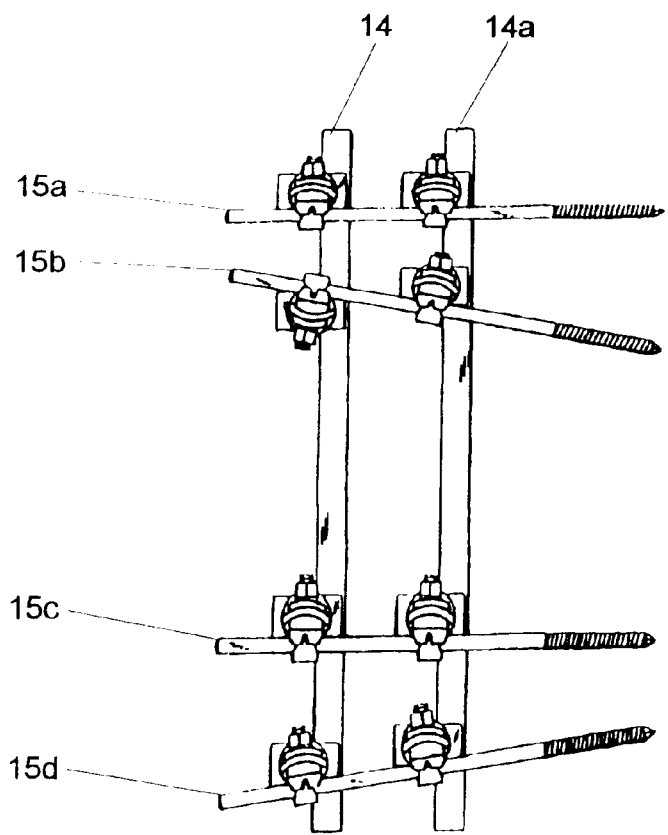
FIG. 1 shows a number of uniform clamping connections of the coupling disks of an external fixator with cylindrical guide rods and screws according to Schanz.

According to the present invention, there is provided for a clamping connection for medical equipment and apparatus. A multilatent static impression coupling with an undivided force-form match comprises two coupling sides 1, 2 with in each case immediately oppositely disposed coupling disks 3, 3' and/or 4, 4 of metallic surfaces. A three-dimensional grain layer 5 and/or 5' of diamond or crystalline boron nitride is solidly attached in each case to one of the coupling disks facing each other, such that the coupling disks are undividedly force-matching based on the surfaces facing each other, and in that the in each case uncoated surface assumes temporarily the respective plastic inversion profile 6 and/or 6' of the three-dimensional grain layer 5 and/or 5' of the each case coated surface, and the immediately oppositely disposed coupling disks are simultaneously undividedly shape-matchingly coupling forming based on external static clamping forces F and/or F' acting in each case on the two coupling disks 3, 3' and/or 4, 4'.

The immediately oppositely disposed surfaces of the coupling disks 3, 3' and/or 4, 4' can be disposed constantly planar parallel relative to each other.

The surfaces of the coupling disks 3, 3' and/or 4, 4' can be formed planar and without profile.

In each case one of the surfaces of the coupling disks 3, 3' and/or 4, 4' is formed as an annular ring. The in each case annular ring-shaped surface of the coupling disk 3, 4 and/or 3', 4' can exhibit a centered inner collar 8. A compression spring element 7 and/or 9 can be supported in the centered inner collar and presses perpendicular to the surface plane. The untensioned axial length L of the compression spring element 7 and/or 9 can be larger than the axial length T of the centered inner collar 8.

The three-dimensional grain layer 5 and/or 5' of the in each case coated coupling disks 3 and/or 4 can exhibit a larger hardness than the uncoated surface of the in each case corresponding coupling disks 3' and/or 4'. The three-dimensional grain layer 5 and/or 5' can exhibit a three-dimensional surface having a chaotic structure.

Corresponding mechanical means 16 can be connected to the coupling sides 1 and/or 2. The position of the corresponding mechanical means 16 can be determined by the coupling-forming coupling disks 3, 3' and/or 4, 4'. The mechanical means 16 can be formed of open clamping jaws 12, 12' and/or of open half boreholes 13. Cylindrical guide rods 14, 14a and/or screws 15a, 14b, 15c, 15d according to Schanz can be fixed and attached in the open half boreholes 13 parallel to the coupling plane.

A mechanical means with a static clamping force F and/or F', directed to the coupling disks disposed in each case facing each other, can be disposed perpendicular to the plane of the coupling disks 3, 3' and/or 4, 4'. The mechanical means 16 can cooperate with cylindrical stay bolts 17 and/or 17'. Closure nuts 11 and/or 11' can support themselves at the cylindrical stay bolts 17 and/or 17'.

Figure 2:
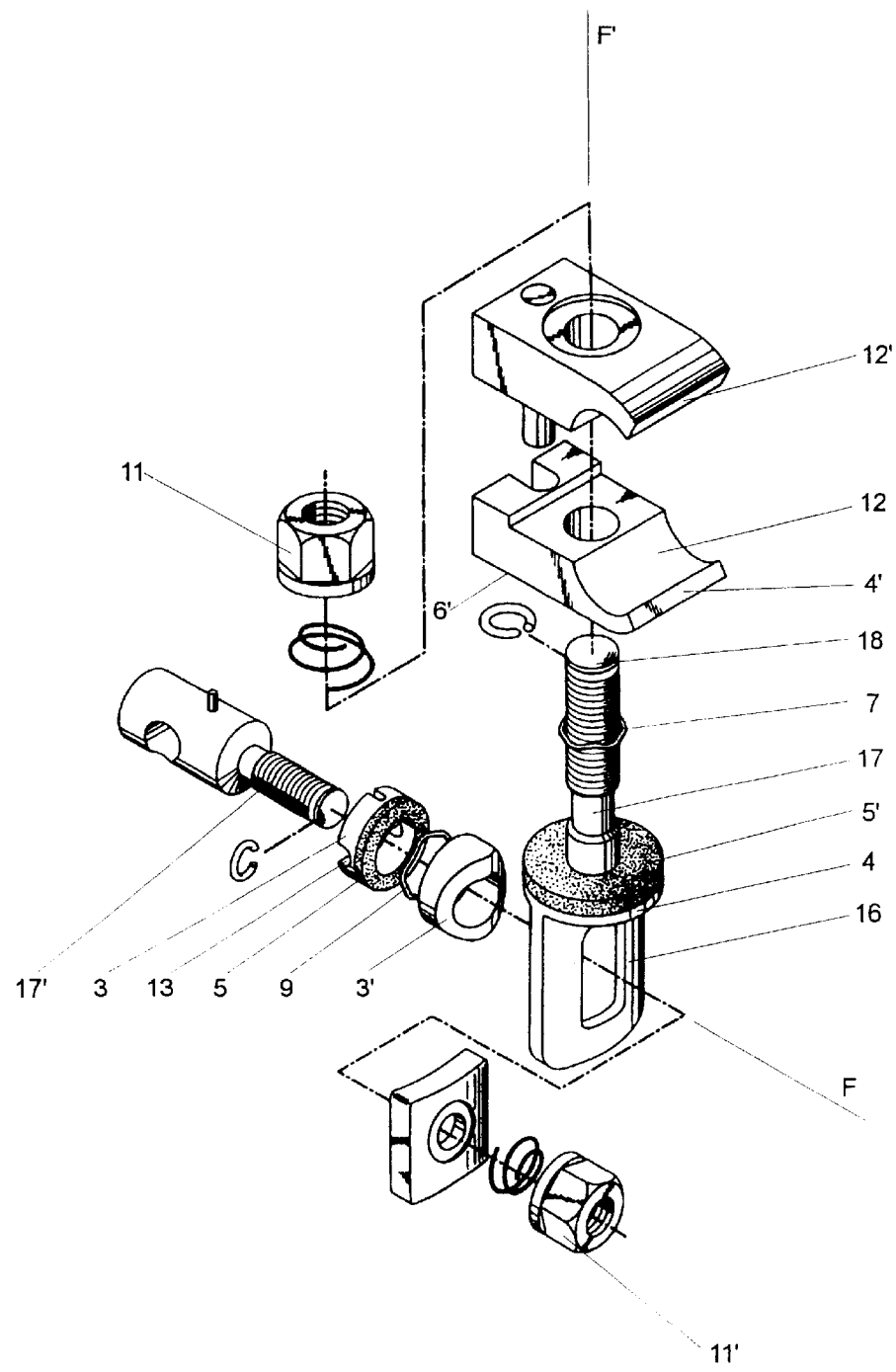
FIG. 2 shows two clamping connections of an external fixator in an exploded view.

The two coupling sides 1, 2 of an external fixator according to FIG. 3 are detachably connected by two adequate clamping connections, disposed in series and referring to the present invention, of in each case two coupling disks 3,3' and 4,4' according to FIG. 2 and disposed plane parallel towards each other.

The coupling sides 1, 2, for example the selectable elements of the coupling side 1a, 1b, 1c, and 1d represented in a final operating position in the fragment, as well as the coupling side 2, for example the selectable elements of the coupling side 2e, 2f, 2g, and 2h represented in the operating position relative to the coupling side 1, are formed on the end side of a plurality of conventional cylindrical guide rods 14, 14a on the one hand and of a number of conventional screws according to Schanz, for example 15a, 15b, 15c, and 15d on the other hand.

The screw according to Schanz is generally a nail for external fixation device such as described for example in the printed patent publication PCT WO 93/22983 to Moroni et al. of Nov. 25, 1993.

The open clamping jaws 12 and 12' according to FIG. 2 are clampable with closure nuts 11, 11' and by partially surrounding in a longitudinally movable way the cylindrical guide rods 14, 14a.

The cylindrical stay bolt 17 carries multi-axially movable mechanical means 16 according to FIG. 2 coaxially to the open clamping jaws 12 and 12', which mechanical means 16 in turn receive the screws 15a, 15b, 15c, and 15d according to Schanz in an open half bore 13 in a tensionable way. One of the respective two metallic surfaces of the coupling disks 3, 3' and/or 4, 4' are solidly coated with a diamond grain layer 5 and/or 5', which diamond grain layer 5 and/or 5' impresses its plastic inverse profile 6 and/or 6' in each case temporarily onto the complementary, uncoated surface under the static clamping force F and/or F' according to FIG. 2 engaging substantially perpendicular to the coupling disks. The surface of the grain layer 5 and of the plastic inverse profile are preferably planar surfaces, but can also be geometrically symmetrical surfaces such as spherical, cylindrical or elliptical surfaces.

The grain layer 5 and/or 5' advantageously is applied to a chromium nickel layer 10 of the respective coupling disks.

The process of applying a diamond coating to a metal is described in the German printed patent document DE-OS 32 01 616 Al based on United States priority application Ser. No. 227,196. Page 10, first paragraph, of the description gives details for the production of such a diamond coating of a medical gripper instrument. The coated surfaces are impressed with a layer of a very fine diamond dust having a grain size from about 10 micrometers to 60 micrometers, such as diamond dust passed through a sieve having an open mesh of 44 micrometers and having an average grain size diameter of 45 micrometers. The impressing or binding of the diamond dust on a metal substrate is known and the binder can be a metal binding agent, a glass binding agent or a plastic resin binding agent, compare for example Davidson, "Handbook of Precision Engineering", Volume 3, McGraw-Hill, 1966, pp. 224 through 254. The process of applying the diamond layer can be described as a lining, a cladding or a plating.

Figure 5A:
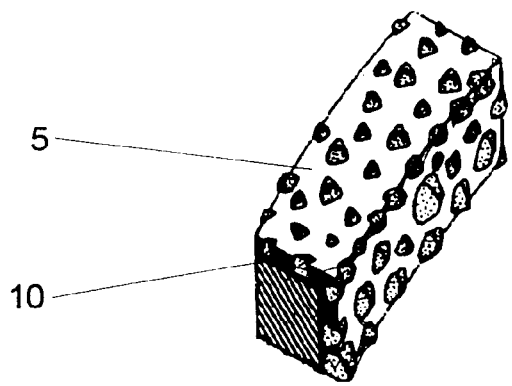
FIG. 5a shows a section of the clamping connection of the present invention according to FIG. 5.
Figure 5:
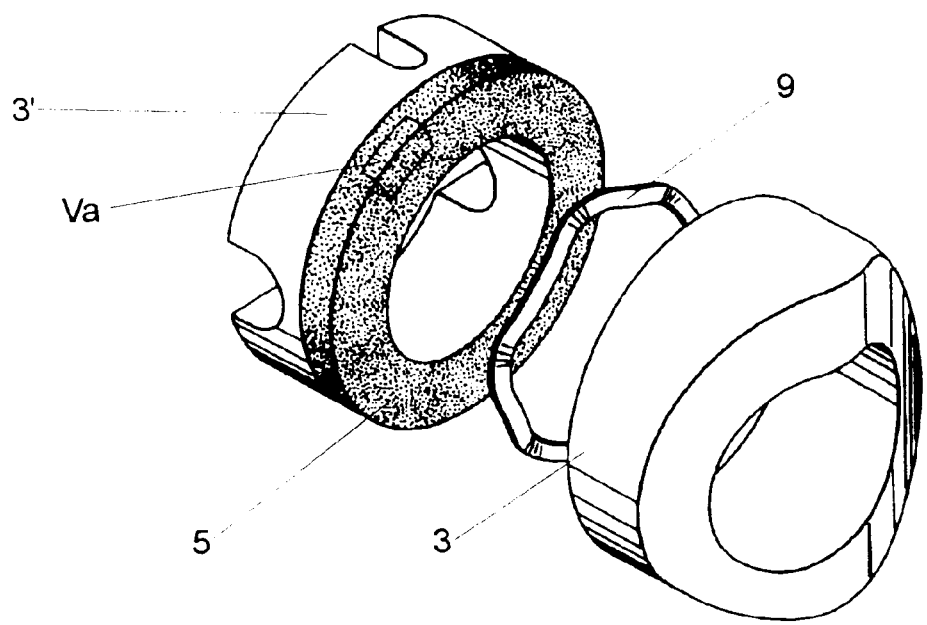
FIG. 5 shows the clamping connection according to the present invention of two metallic surfaces of coupling disks in an unclamped position.
Figure 6:
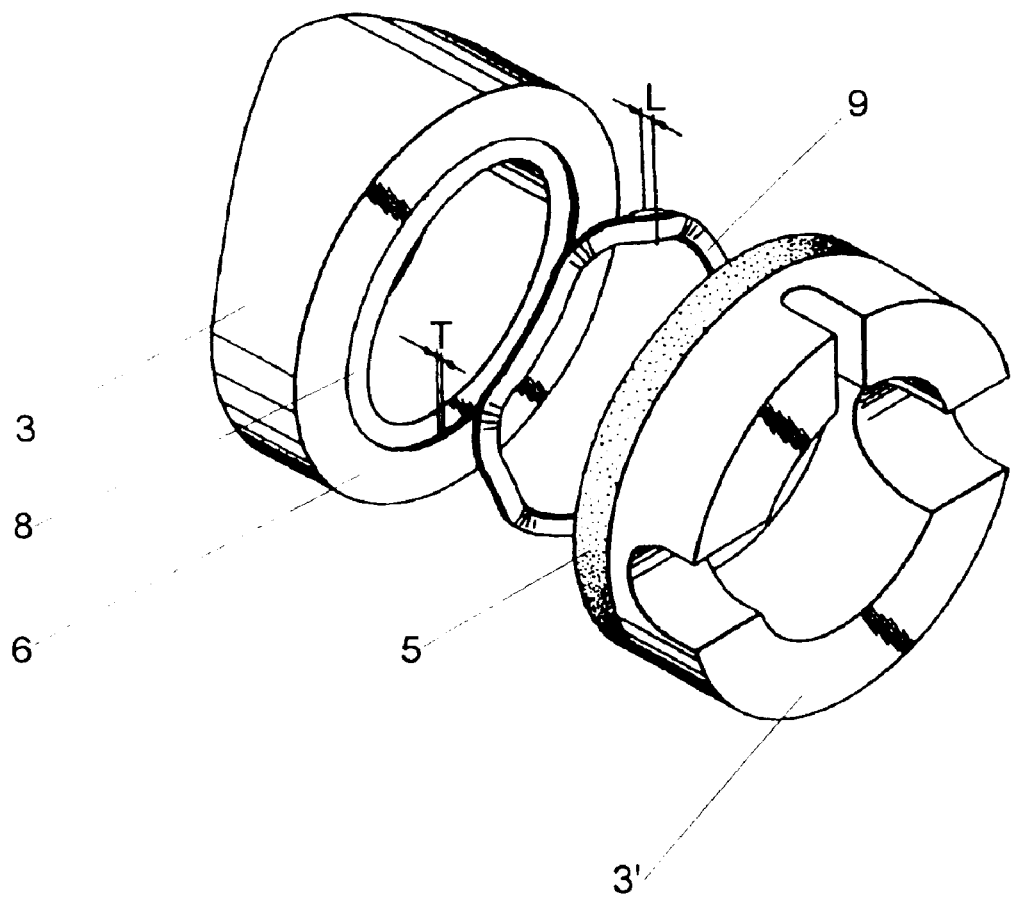
FIG. 6 shows the clamping connection of the present invention of two metallic surfaces in a corresponding perspective relative to FIG. 5.

The in each case uncoated surface of the respective coupling disks 3, 3' and/or 4, 4' is finally equipped with a central inner collar 8 of the axial length T according to FIG. 5 and FIG. 6, wherein in each case a compression spring element 7 and/or 9 (FIG. 2) of the untensioned length L is centrally supported in the central inner collar 8.

The compression spring elements 7 and 9 are furthermore supported by the coupling disks 3, 3' and/or 4, 4' at for example mechanical means 16' and/or for example an open clamping jaw 12 by cylindrical stay bolts 17, 17' engaging closure nuts 11 and/or 11', whereby the clamping forces F and/or F' are measured continuously and are opposing the compression spring element 7 and/or 9 and thereby support the undelayed opening of the clamping connection after disengaging the closure nuts 11 and 11'.

Based on this respective impression of the grain layers 5 and/or 5', there is produced a point-precise, absolutely tension-free clamping connection of the coupling disks 3, 3' and/or 4, 4', wherein this multilatent force-form match, for practical purposes, is free of wear and indefinitely repeatable.

The open thread end 18 of the cylindrical stay bolt 17 is available thereby for the screwing on of another or of an additional closure nut, such as perhaps a specific cap nut as a length gauge for a controllable opening measure of the clamping of the cylindrical guide rods 14, 14a for the purpose of a secure dynamization of the fracture.

Figure 4A:
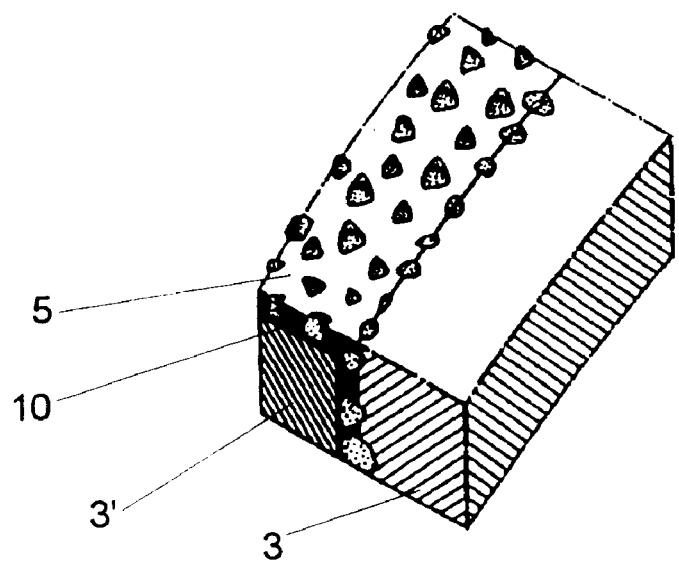
FIG. 4a shows a section of the clamping connection of the present invention according to FIG. 4.
Figure 4:
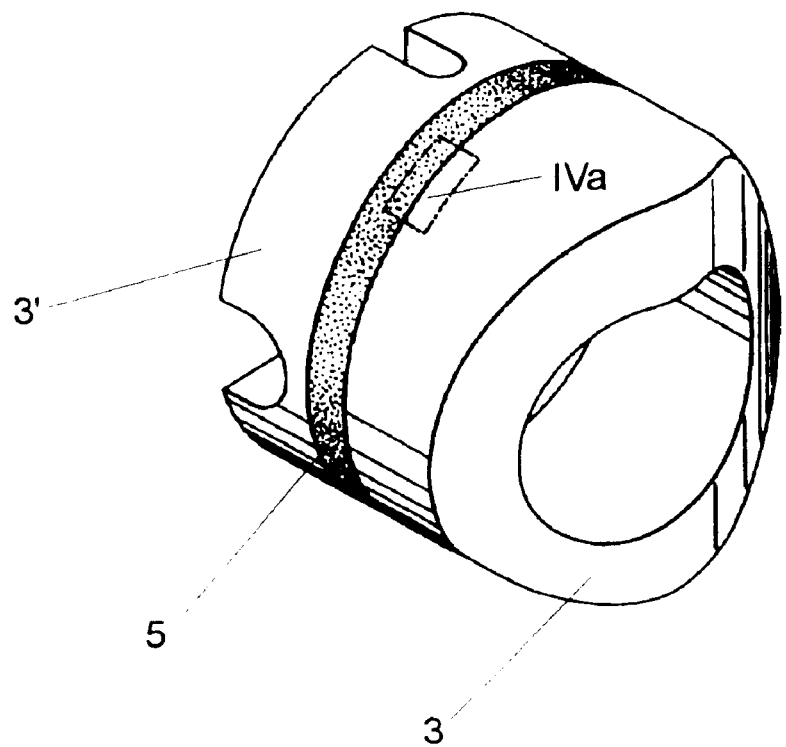
FIG. 4 shows a clamping connection according to the present invention of two metallic surfaces of coupling disks in clamped position.

FIGS. 4a and 5a show thereby again the core of the invention as the sections IVa and Va of the diamond-coated coupling disks 3 and 5 according to FIG. 4 and FIG. 5.

The essence of the clamping connection according to the present invention for medical equipment and apparatus thus comprises that the diamond grain layer of a metallic surface impresses shape-matchingly and repeatably "de novo" the respective authentic inversion of its plastic profile, when subjected to a static force acting about perpendicular to the face plane, to a predominantly planar-parallel, uncoated surface.

This internal point-precise, stable and completely tension-free impression of the grain layer 5 and/or 51 according to the present invention assures thus an internal point-precise, stable and completely tension-free clamping connection of the two coupling sides 1 and 2, as defined in the object of the invention.

The preconditions of a complication-free external osteosynthesis, in particular in connection with an external fixator with frames of cylindrical guide rods 14, 14*a*, are thus created according to the invention in a simple and very practical construction.

It will be understood that each of the elements described above, or two or more together, may also find a useful application in other methods and types of clamping devices differing from the types described above.

While the invention has been illustrated and described as embodied in the context of a clamping connection for medical equipment and apparatus, it is not intended to be limited to the details shown, since the various modifications and structural changes may be made without departing in any way from the spirit of the present invention.

Without further analysis, the foregoing will so fully reveal the gist of the present invention that others can, by applying current knowledge, readily adapt it for various applications without omitting features that, form the standpoint of prior art, fairly constitute essential characteristics of the generic or specific aspects of this invention.

What is claimed as new and desired to be protected by Letters Patent is set forth in the appended claims:

1. A clamping connection for medical supports comprising:
   a first coupling disk having a first engaging metallic face and a three-dimensional grain layer of diamond or crystalline boron nitride limited with a first surface of the first coupling disk;
   a second coupling disk having a second engaging metallic face and a second uncoated metallic surface wherein the first coupling disk with the first surface facing the second uncoated metallic surface of the second coupling disk are undividedly force-matching coupled and wherein the second uncoated metallic surface assumes temporarily a respective plastic inversion profile of the first surface of the three-dimensional grain layer, and wherein the first coupling disk and the second coupling disk form an undividedly shape-matchingly coupling based on external static clamping forces pressing the first coupling disk against the second coupling disk and form a multilatent static impression coupling with an undivided force-form match.

2. The clamping connection according to claim 1,
   wherein the first surface of the first coupling disk and the second uncoated metallic surface of the second coupling disk are disposed constantly planar parallel relative to each other.

3. The clamping connection according to the claim 1,
   wherein the first surface of the first coupling disk is formed planar and without profile and wherein the second uncoated metallic surface of the second coupling disk is formed planar and without profile.

4. The clamping connection according to claim 1,
   wherein the first surface of the first coupling disk is formed as an annular ring.

5. The clamping connection according to claim 4,
   wherein the first surface of the first coupling disk exhibits a centered inner collar and wherein a compression spring element is supported in the centered inner collar and presses perpendicular to a surface plane, and wherein an untensioned axial length of the compression spring element is larger than an axial length of the centered inner collar.

6. The clamping connection according to claim 1,
   wherein the second uncoated metallic surface of the second coupling disk is formed as an annular ring.

7. The clamping connection according to claim 6,
   wherein the second uncoated metallic surface of the second coupling disk exhibits a centered inner collar and wherein a compression spring element is supported in the centered inner collar and presses perpendicular to a surface plane, and wherein an untensioned axial length of the compression spring element is larger than an axial length of the centered inner collar.

8. The clamping connection according to claim 1,
   wherein the three-dimensional grain layer of the first coupling disk exhibits a larger hardness than the second uncoated surface of the second coupling disk, and wherein the three-dimensional grain layer exhibits a three-dimensional surface having a chaotic structure.

9. The clamping connection according to claim 1 further comprising p1 mechanical means attached to the first coupling disk, wherein a position of the mechanical means is determined by the undividedly shape-matchingly coupling formed by the first coupling disk and second coupling disk.

10. The clamping connection according to claim 9,
    wherein the mechanical means are formed of open clamping jaws;
    wherein cylindrical guide rods are fixed and attached in the open clamping jaws parallel to a coupling plane.

11. The clamping connection according to claim 9,
    wherein the mechanical means are formed of open clamping jaws;
    wherein screws according to Schanz are fixed and attached in the open clamping jaws parallel to a coupling plane.

12. The clamping connection according to claim 9,
    wherein the mechanical means are formed of open half boreholes,
    wherein cylindrical guide rods are fixed and attached in the open half boreholes parallel to a coupling plane.

13. The clamping connection according to claim 9,
    wherein the mechanical means are formed of open half boreholes;
    wherein screws according to Schanz are fixed and attached in the open half boreholes parallel to a coupling plane.

14. The clamping connection according to claim 1 further comprising mechanical means connected to the second coupling disk, wherein a position of the mechanical means is determined by the undividedly shape-matchingly coupling formed by the first coupling disk and second coupling disk.

15. The clamping connection according to claim 14,
    wherein the mechanical means are formed of open clamping jaws;
    wherein cylindrical guide rods are fixed and attached in the open clamping jaws parallel to a coupling plane.

16. The clamping connection according to claim 14,
wherein the mechanical means are formed of open clamping jaws;
wherein screws according to Schanz are fixed and attached in the open clamping jaws parallel to a coupling plane.

17. The clamping connection according to claim 14,
wherein the mechanical means are formed of open half boreholes;
wherein cylindrical guide rods are fixed and attached in the open half boreholes parallel to a coupling plane.

18. The clamping connection according to claim 14,
wherein the mechanical means are formed of open half boreholes,
wherein screws according to Schanz are fixed and attached in the open half boreholes parallel to a coupling plane.

19. The clamping connection according to claim 1 further comprising
mechanical means delivering a static clamping force directed to the first coupling disk and the second coupling disk disposed facing each other, wherein the mechanical means is disposed perpendicular to a plane of engaging faces of the first coupling disk and the second coupling disk.

20. The clamping connection according to claim 19 further comprising
a cylindrical stay bolt, wherein the mechanical means cooperate with the cylindrical stay bolt; and
a closure nut supported at the cylindrical stay bolt.

21. A clamping connection for medical equipment and apparatus comprising
a first coupling disk (3 and/or 4) having a first metallic surface;
a three-dimensional grain layer (5 and/or 5') of diamond or crystalline boron nitride having a first grain surface and a second grain surface and solidly attached at the first grain surface of the three-dimensional grain layer (5 and/or 5') to the first coupling disk at a side oppositely disposed to the first metallic surface of the first coupling disk (3 and/or 4);
a second coupling disk (3' and/or 4') having a second metallic surface and an uncoated surface disposed facing the second grain surface of the three-dimensional grain layer (5 and/or 5') wherein the uncoated surface of the second coupling disk assumes temporarily a plastic inversion profile (6 and/or 6') of the second grain surface of the three-dimensional grain layer (5 and/or 5') when the first coupling disk and the second coupling disk are undividedly shape-matchingly coupled based on external static clamping forces (F and/or F') acting on the first coupling disk and the second coupling disk (3, 3' and/or 4, 4').

22. The clamping connection for medical equipment and apparatus according to claim 21,
wherein the second grain surface of the three-dimensional grain layer (5 and/or 5') and the uncoated surface of the second coupling disk are disposed constantly planar parallel relative to each other.

23. The clamping connection for medical equipment and apparatus according to the claim 21,
wherein the second grain surface of the three-dimensional grain layer (5 and/or 5') and the uncoated surface of the second coupling disk are formed planar and without profile.

24. The clamping connection for medical equipment and apparatus according to claim 21,
wherein at least one of the second grain surface of the three-dimensional grain layer (5 and/or 5') and the uncoated surface of the second coupling is formed as an annular ring and wherein at least one of the second grain surface of the three-dimensional grain layer (5 and/or 5') and the uncoated surface of the second coupling disk exhibits a centered inner collar (8), wherein a compression spring element (7 and/or 9) is supported in the centered inner collar and presses perpendicular to the surface plane, wherein an untensioned axial length (L) of the compression spring element (7 and/or 9) is larger than an axial length (T) of the centered inner collar (8).

25. The clamping connection for medical equipment and apparatus according to claim 21,
wherein the three-dimensional grain layer (5 and/or 5') exhibits a larger hardness than the uncoated surface of the second coupling disk (3' and/or 4'), and wherein the three-dimensional grain layer (5 and/or 5') exhibits a three-dimensional surface having a chaotic structure.

26. The clamping connection for medical equipment and apparatus according to claim 21,
wherein mechanical means (16) are attached to at least one of the first coupling disk and the second coupling disk and wherein a position of the mechanical means (16) is determined by the first coupling disk and the second coupling disk (3, 3' and/or 4, 4'), and wherein the mechanical means (16) are formed of open clamping jaws (12, 12') and/or of open half boreholes (13), and wherein cylindrical guide rods (14, 14a) and/or screws (15a, 14b, 15c, 15d) according to Schanz are fixed and attached in the open half boreholes (13) parallel to a plane of the first coupling disk and the second coupling disk.

27. The clamping connection for medical equipment and apparatus according to claim 21,
wherein mechanical means with a static clamping force (F and/or F'), directed to the first coupling disk and the second coupling disk are disposed perpendicular to a plane of the first coupling disk and the second coupling disk (3, 3' and/or 4, 4') and wherein the mechanical means (16) cooperate with cylindrical stay bolts (17 and/or 17'), and wherein closure nuts (11 and/or 11') support themselves at the cylindrical stay bolts (17 and/or 17').

28. A clamping connection for medical supports comprising:
a first coupling disk having a three-dimensional grain layer of diamond or crystalline boron nitride solidly attached to an engaging metallic face of the first coupling disk and forming a first surface of the first coupling disk;
a second coupling disk lacking a three-dimensional grain layer of diamond or crystalline boron nitride solidly attached to a second engaging metallic face of the second coupling disk, said first coupling disk with the first surface facing the second engaging metallic face of the second coupling disk such that the coupling disks are completely force-transferring based on the first surface facing the second engaging metallic face and in that the second engaging metallic face assumes temporarily a respective plastic inversion profile of the three-dimensional grain layer of the first surface, and wherein the first coupling disk disposed immediately oppositely and the second coupling disk are simultaneously completely shape-matchingly coupled based on external static clamping forces pressing the first coupling disk against the second coupling disk and form a multilatent static impression coupling with an undivided force-form match.

* * * * *